(12) United States Patent
Beck et al.

(10) Patent No.: US 8,718,742 B2
(45) Date of Patent: May 6, 2014

(54) INTEGRATED WIRELESS PATCH FOR PHYSIOLOGICAL MONITORING

(75) Inventors: James Beck, Berkeley, CA (US); Venkateswara R. Sattiraju, Union City, CA (US); Ali M. Niknejad, Berkeley, CA (US); Louis C. Yun, Los Altos, CA (US); Randall Lee, Hillsborough, CA (US); Surendar Magar, Dublin, CA (US); Lois M. Fisher, San Francisco, CA (US)

(73) Assignee: HMicro, Inc., Los Altos, CA (US)

( * ) Notice: Subject to any disclaimer, the term of this patent is extended or adjusted under 35 U.S.C. 154(b) by 506 days.

(21) Appl. No.: 12/601,373

(22) PCT Filed: May 23, 2008

(86) PCT No.: PCT/US2008/064800
§ 371 (c)(1),
(2), (4) Date: Aug. 27, 2010

(87) PCT Pub. No.: WO2008/148067
PCT Pub. Date: Dec. 4, 2008

(65) Prior Publication Data
US 2010/0317958 A1    Dec. 16, 2010

Related U.S. Application Data

(60) Provisional application No. 60/940,072, filed on May 24, 2007.

(51) Int. Cl.
*A61B 5/0408* (2006.01)
*A61B 5/0402* (2006.01)

(52) U.S. Cl.
USPC .......................................... 600/393; 600/391

(58) Field of Classification Search
USPC ................................................. 600/391–393
See application file for complete search history.

(56) References Cited

U.S. PATENT DOCUMENTS 3,786,391 A    1/1974   Mathauser
3,808,577 A    4/1974   Mathauser
(Continued)

FOREIGN PATENT DOCUMENTS

WO    WO 01/78594 A1    10/2001
WO    WO 02/089667 A1   11/2002
(Continued)

OTHER PUBLICATIONS

International search report and written opinion dated May 28, 2009 for PCT Application No. US08/80695.

(Continued)

*Primary Examiner* — Lee S Cohen
(74) *Attorney, Agent, or Firm* — Wilson Sonsini Goodrich & Rosati (57) ABSTRACT

A sensor system in accordance with the present invention comprises a plane member, a plurality of electrodes within the plane member, adapted to contact a human body to detect and monitor human generated voltages. The sensor can be applied to monitor a variety of applications relating to health, disease progression, fitness and wellness. Some of the specific applications include the monitoring of ECG, EEG, EMG, glucose, electrolytes, body hydration, dehydration, tissue state and wounds. Various aspects of the invention are shown by illustrating certain embodiments. Many other embodiments can be used to implement the invented schemes.

8 Claims, 8 Drawing Sheets

(56) References Cited

U.S. PATENT DOCUMENTS

| | | | |
|---|---|---|---|
| 4,067,342 A | | 1/1978 | Burton |
| 4,082,086 A | * | 4/1978 | Page et al. ............... 600/391 |
| 4,084,583 A | * | 4/1978 | Hjort ....................... 600/544 |
| 4,121,573 A | * | 10/1978 | Crovella et al. .......... 600/382 |
| 4,365,634 A | * | 12/1982 | Bare et al. ............... 600/391 |
| 4,398,545 A | * | 8/1983 | Wilson ..................... 607/152 |
| 4,653,503 A | | 3/1987 | Heath |
| 5,372,125 A | | 12/1994 | Lyons |
| 5,578,065 A | | 11/1996 | Hattori et al. |
| 5,895,369 A | | 4/1999 | Flower |
| 6,441,747 B1 | | 8/2002 | Khair et al. |
| 6,456,720 B1 | | 9/2002 | Brimhall et al. |
| 6,897,788 B2 | | 5/2005 | Khair et al. |
| 6,965,794 B2 | * | 11/2005 | Brody ....................... 600/546 |
| 7,156,301 B1 | | 1/2007 | Bonalle et al. |
| 7,257,438 B2 | | 8/2007 | Kinast |
| 7,668,580 B2 | * | 2/2010 | Shin et al. ............... 600/391 |
| 7,969,307 B2 | | 6/2011 | Peeters |
| 7,970,450 B2 | * | 6/2011 | Kroecker et al. ......... 600/391 |
| 2003/0040305 A1 | | 2/2003 | Ng et al. |
| 2006/0009691 A1 | * | 1/2006 | Yeo et al. ................. 600/386 |
| 2006/0155183 A1 | | 7/2006 | Kroecker et al. |
| 2006/0264767 A1 | | 11/2006 | Shennib |
| 2007/0060832 A1 | | 3/2007 | Levin |
| 2007/0072443 A1 | | 3/2007 | Rohrbach et al. |
| 2007/0093705 A1 | | 4/2007 | Shin et al. |
| 2007/0179376 A1 | * | 8/2007 | Gerder ..................... 600/393 |
| 2008/0309287 A1 | | 12/2008 | Reed |
| 2009/0036792 A1 | * | 2/2009 | DeLuca et al. ............ 600/546 |
| 2010/0326703 A1 | | 12/2010 | Gilad et al. |
| 2011/0028822 A1 | | 2/2011 | Beck et al. |
| 2011/0062241 A1 | | 3/2011 | Beck et al. |
| 2011/0065476 A1 | | 3/2011 | Hsiao et al. |

FOREIGN PATENT DOCUMENTS

| | | |
|---|---|---|
| WO | WO 03/065926 A2 | 8/2003 |
| WO | WO 03/065926 A3 | 6/2004 |
| WO | WO 2005/094674 A1 | 10/2005 |
| WO | WO 2006/061354 A1 | 6/2006 |
| WO | WO 2007/060609 A2 | 5/2007 |
| WO | WO 2007/060609 A3 | 10/2007 |
| WO | WO 2008/006150 A1 | 1/2008 |

OTHER PUBLICATIONS

International search report and written opinion dated Jul. 20, 2009 for PCT Application No. US08/80659.
International search report and written opinion dated Sep. 29, 2008 for PCT Application No. US08/64800.
Office action dated Jun. 26, 2012 for U.S. Appl. No. 12/739,561.
Office action dated Nov. 21, 2012 for U.S. Appl. No. 12/739,553.
Office action dated Jul. 30, 2013 for U.S. Appl. No. 12/739,553.
U.S. Appl. No. 14/091,252, filed Nov. 26, 2013, Beck.

* cited by examiner

Figure 1: A Typical MHc System

Figure 2a: One Embodiment of Multiple Electrode Scheme

*Figure 3a: One Embodiment of Electronics Connected to Electrode*

*Figure 3b: One Embodiment of Electronics for Multi-Electrode Scheme*

*Figure 3c: A More Flexible Embodiment for Multi-Electrode Scheme*

Figure 4: Fully Disposable Patch Build

Figure 5: Partially Reusable Patch Build

Figure 6a: ECG Views using Opposite Electrode Pairs

ECG Leads (Views)
Six Limb Lead Coverage – Vertical

Figure 6A:
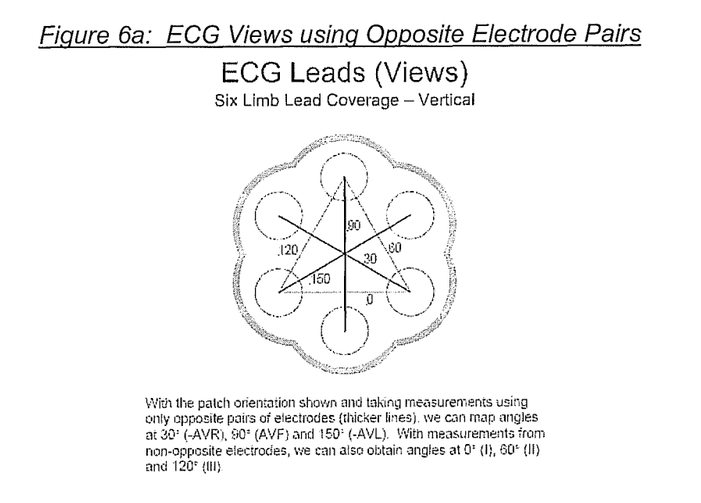
FIG. 6a is an illustration of ECG views using opposite electrode pairs.

With the patch orientation shown and taking measurements using only opposite pairs of electrodes (thicker lines), we can map angles at 30° (-AVR), 90° (AVF) and 150° (-AVL). With measurements from non-opposite electrodes, we can also obtain angles at 0° (I), 60° (II) and 120° (III).

Figure 6b: ECG Views by using Alternate Electrode Pairs

ECG Leads (Views)
Six Limb Lead Coverage – Horizontal

Figure 6B:
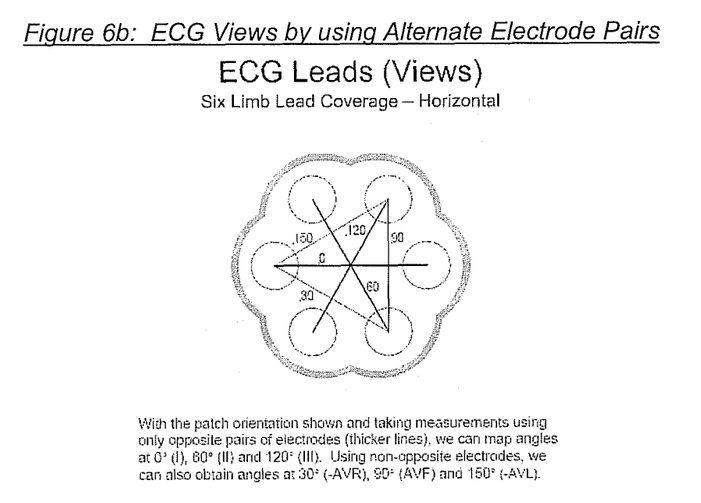
FIG. 6b is an illustration of ECG views using alternate electrode pairs.

With the patch orientation shown and taking measurements using only opposite pairs of electrodes (thicker lines), we can map angles at 0° (I), 60° (II) and 120° (III). Using non-opposite electrodes, we can also obtain angles at 30° (-AVR), 90° (AVF) and 150° (-AVL).

*Figure 7: Graphic Aid to Attach the patch to the body*

Orientation Graphic Aid

With the "heart" right side up, opposite
electrodes will pick up leads I, II and III

INTEGRATED WIRELESS PATCH FOR PHYSIOLOGICAL MONITORING

FIELD OF THE INVENTION

The present invention relates generally to a wireless healthcare system and more particularly to sensors utilized with such a system.

BACKGROUND OF THE INVENTION

Figure 1:
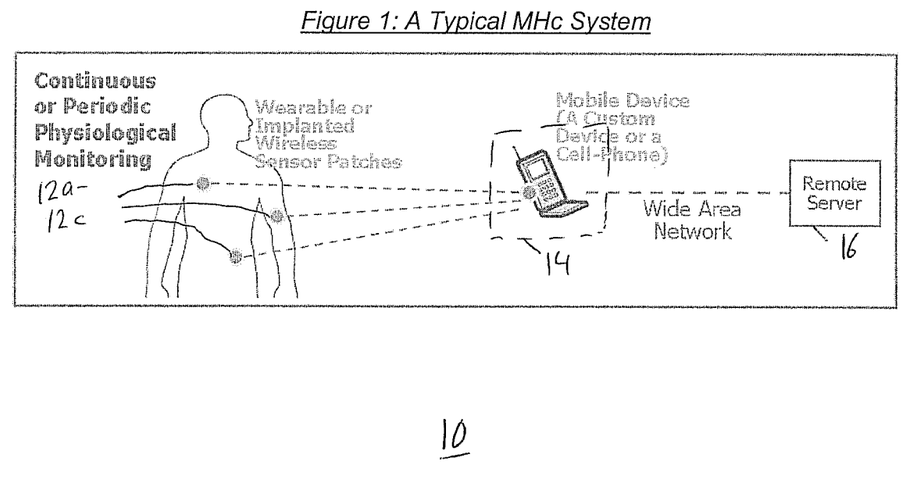
FIG. 1 is an illustration of a wireless healthcare monitoring system.

Wireless healthcare systems, referred to as WHc systems are being used increasingly to help reduce healthcare costs, increase patient independence and provide better outcomes. FIG. 1 is a simple block diagram of a WHc system 10. The WHc system includes three main elements: wireless sensors 12a-12n, a host monitor 14, and a remote server 16. Wireless Sensors 12a-12n measure elements and the physiological signals from the body and wirelessly transmit them to a nearby device, as a host monitor 14 in FIG. 1. A host monitor 14 receives the signals and can relay them to a remote server 16 via a cellular or other type of network. The host monitor 14 could be a cell phone, portable monitor, catheter, or tissue sampling system, or the device could also be a laboratory instrument, such as a portable analyzer, point of care test kit, or any other laboratory instrument system. A host monitor 14 could be a stationary device such as a hospital bedside patient monitor, a point of care test kit or a lab instrument. The host monitor 14 could also be a portable device such as holter monitor, a glucose meter or a compact patient monitor. In emerging WHc systems 10, the host monitor 14 could be a mobile device such as a cell phone or a personal digital assistant. In all these cases the host monitor 14 can have the capability to collect data from wireless sensors 12a-12n and to perform clinical analysis on the data. The host monitor 14 could also be simply a wireless gateway or access point that collects physiological data from wireless sensors 12a-12n and simply transmit it to remote server 16 for clinical analysis. In some cases, the wireless sensors 12a-12n can have on-board processors to perform clinical analysis and occasionally communicate with the host monitor 14 and/or remote server 16.

In general, progress has been made by industry to make the host monitors 14 smaller, more capable and providing flexible networking connectivity (e.g. wireless) with remote servers 16. However, wireless sensors 12a-12n still remains a major problem. Therefore, in most cases, the patients remain tethered to host monitors, wearing traditional physiological sensors that are sending data to host monitors through wires. It is important to create effective wireless sensors 12a-12n to enable wide deployment of wireless healthcare.

Physical Monitoring

Many variables of physiological significance are measured as voltage signals (e.g. ECG, EEG, EMG, continuous glucose monitoring, electrolytes). The signals may be measured via electrodes placed variously on, within, or near a biological sample or, alternatively, integrated into a testing device. Electrodes may be placed on the skin, mounted on catheters, placed within the vascular or urinary system, inserted into biological tissue, or integrated into other devices such as invasive micromechanical devices or external analytical instrumentation used to evaluate samples of biological tissue or fluids. An electrode is a conducting connector between a biological sample and an electronic circuit, where the biological sample may be skin, tissue, blood or blood components, interstitial fluid, or urine. The material used for surface electrodes is typically silver or a silver compound which may be covered with an electrolyte for enhanced conductivity. Materials used in other sensors may vary to support sensors linked to highly specific reagents such as ion-specific resins or gels, various immunoassay formats mounted on a substrate, electrochemical or crystalline systems, or other types of diagnostic testing schemes.

Analysis of the physiological signals may be performed by any of the three devices in the system to extract the information about a person's health state—sensor 12a-12n, host monitor 14 or remote server 16. Data may alternatively be stored and later displayed for analysis by a human or computer. Analysis can also be performed in a distributed fashion, jointly by any combination of these three devices.

Wireless Sensors

Wireless sensors 12a-12n typically include one or more electrodes. What is meant by a sensor is a device containing one or more electrodes which may be placed on the skin, mounted on catheters, placed within the vascular or urinary system, inserted into biological tissue, or integrated into other devices such as invasive micromechanical devices or external analytical instrumentation used to evaluate samples of biological tissue or fluids. Furthermore, the sensor could be a patch for the surface of the skin or an implantable sensor embedded in the body.

Wireless sensors 12a-12n need to have very small form factors to accommodate patient convenience and comfort, ease-of-use and ease-of-integration into small systems. Wireless sensors 12a-12n should also be low cost, particularly if used as a disposable. These requirements call for a design that is highly integrated in every respect, including the electrode structure. To date, wireless sensors 12a-12n have been bulky, power-hungry, expensive and difficult to use.

Also, the lead placement scheme of many previous physiological measurement procedures (e.g. 12-lead ECG) is not well suited to compact integrated wireless systems. Many such systems were developed decades ago based on the electronic components available at that time and the wired connectivity. Today's electronic components are far more precise which can resolve much smaller signals from the body. The wireless connectivity also alleviates the noise picked up by long wires in wired sensor systems. Therefore, migration to wireless systems avails a fresh opportunity to create a new class of compact wireless sensors that can displace traditional bulky electrode systems used in applications such as 12-lead ECG. The present invention addresses such a need.

SUMMARY OF THE INVENTION

A sensor patch in accordance with the present invention comprises a plane member, a plurality of electrodes within the plane member, adapted to contact a human body to detect and monitor human generated voltages. The sensor can be applied to monitor a variety of applications relating to health, disease progression, fitness and wellness. Some of the specific applications include the monitoring of ECG, EEG, EMG, glucose, electrolytes, body hydration, dehydration, tissue state and wounds. Various aspects of the invention are shown by illustrating certain embodiments. Many other embodiments can be used to implement the invented schemes.

DETAILED DESCRIPTION OF PREFERRED EMBODIMENTS

The present invention relates generally to a wireless healthcare system and more particularly to sensors utilized with such a system. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

A system and method in accordance with the present invention relates to a method and system in accordance with the present invention for providing integrated wireless sensors. The wireless sensor for use in a wireless healthcare system (Whc) needs the following elements:

Electrodes to sense signals
Electronic circuits to amplify and condition signals
Optional analog to digital (A/D) converter
Processor to manage the signals prior to transmission
Radio for transmission to a nearby mobile device or any other device
Energy source (battery) to power the electronics (add the bullet dot?)
Means to attach the patch to body
Protective covering to withstand environmental hazards In a system and method in accordance with one embodiment of the present invention, a patch with multiple conductive electrodes to make contact with the body to detect and monitor human-generated body voltages is provided. The electrodes are connected to multiple electronic amplifiers and associated filters, etc., which in turn connect to a radio. A patch may include one or more electrodes depending upon the application. In some cases, the various electrodes may be used to measure different variables in the same biological sample or at the same biological interface. In other cases, differential voltages are measured across a pair or pairs of electrodes, where spatial information is important for a single variable, such as ECG and EEG measurements. To describe the features of the present invention in more detail, refer now to the following description in conjunction with the accompanying figures.

As before mentioned, although the embodiments of the present invention described herein refer to patches placed on the skin surface, one of ordinary skill in the art readily recognizes that the present invention can be utilized in a variety of environments where sensors are used. For example, electrodes may be placed on the skin, mounted on catheters, placed within the vascular or urinary system, inserted into biological tissue, or integrated into other devices such as invasive micromechanical devices or external analytical instrumentation used to evaluate samples of biological tissue or fluids.

In one embodiment electrodes are fabricated on the bottom plane of a patch which contacts the body or biological sample. Multiple electrodes can be arranged in a variety of ways— circular array, a rectangular array or a linear array, for example, depending on the desired application. The size and shape of the electrodes and the total number of electrodes may also vary. Trade-offs are made in a given application to achieve the desired specifications for that application.

Figure 2A:
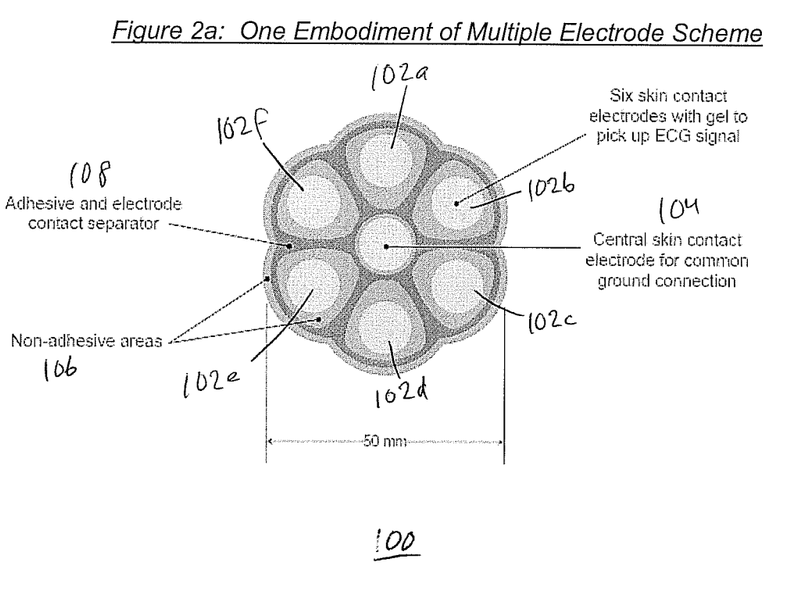
FIG. 2a is a first embodiment of a patch sensor with multiple electrodes in accordance with the present invention.
Figure 2B:
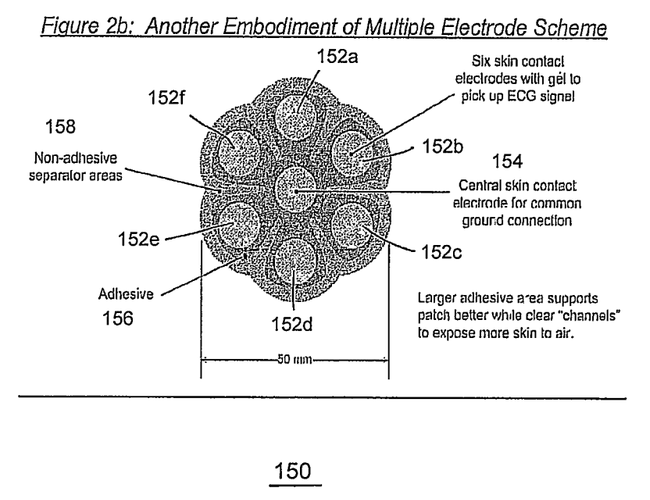
FIG. 2b is a second embodiment of a patch sensor with multiple electrodes in accordance with the present invention.

FIG. 2a represents a first embodiment of a multi-electrode patch 100. FIG. 2b represents a second embodiment of a multi-electrode patch 150. In both embodiments, a plurality of electrodes are arranged in a circular array with an additional electrode placed in the middle of the array. One possible arrangement of the electrodes would be similar to the drawing shown in FIG. 2a. In this particular case, multiple pairs of electrodes 102a-102n in the circular array can be simultaneously sampled to optimally detect differential voltages traveling in any direction.

In this embodiment each of the electrodes 102a-102f are surrounded by non-adhesive areas 106a-106f. There is also an adhesive and electrode contact separator 108 between the non-adhesive areas 106 of the patch 100. In this embodiment, the six skin contact electrodes 102a-102f are used in pairs to provide a differential measurement for the patch. For example, electrode pair 102a-102d would provide one measurement, electrode pair 102b and 102e would provide a second measurement, and electrode pair 102c and 102f would provide a third measurement.

Each of the pairs 102a-102d, 102b-102e, and 102c-102f could be utilized to measure different conditions within the body or they could be utilized to measure one condition or any number in between. Furthermore, there can be as little as two electrodes on the patch or as many as can be placed thereon to provide the differential measurement of signals.

FIG. 2b is similar to FIG. 2a except that each of the electrodes 152a-152f is surrounded by adhesive areas 156 while the separator areas 158 around the electrodes 152a-152f are non-adhesive. The larger adhesive area 154 supports the patch 150 while allowing for a clear channel to expose more skin to air. A central electrode 104 and 154 of FIGS. 2a and 2b, respectively, is used by an electronic circuit (not shown) as the "ground" connection which serves as a reference to help reject unwanted electric signals (noise). The patch 100 could include in an embodiment output devices such as LEDs, displays or an audible tone that may function as warning signals or may signify other conditions to the patient.

Although these embodiments contemplate the measurement of differential voltages across multiple pairs of electrodes, the same structure could be used to support a sensor system using different electrode materials such as gels, resins, or substrates supporting various diagnostic testing methodologies described previously. It should be understood that the electrodes can be in any array and they would be in the scope of the present invention. The number, shape, physical size and arrangement of the electrodes as well as the overall size of its pairs may also vary. The overall size of the patch will vary accordingly. In one embodiment, the contact area of the sensor patch is less than 200 cm². In one embodiment the area of an electrode is less than 10 cm².

Patch or Sensor Electronics

Figure 3A:
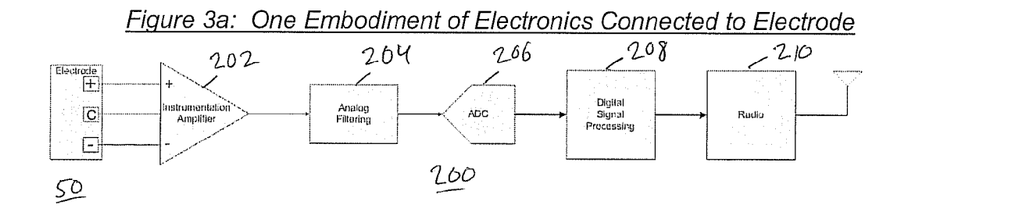
FIG. 3a is an embodiment of a sensor with one electrode and showing a schematic of the electronics processing.

The electronic circuits for a wireless patch will vary by application but will support certain common signal acquisition and conditioning functions. One embodiment of the electronic circuits that need to be connected for a single electrode pair wireless patch is shown in FIG. 3a. As shown, the electronics perform the function of picking up signals from the electrodes, then amplifying, filtering, digitizing and transmitting the signals over a wireless link. The functions shown in the figures may be instantiated with discrete circuits, one or more ASICs (Application Specific Integrated Circuits) or any combination of them.

Figure 3B:
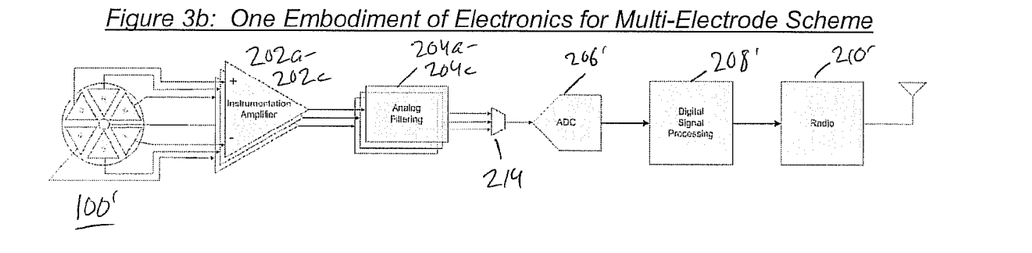
FIG. 3b is a first embodiment of a sensor coupled to multiple electrodes.

The electronics can be modified to connect to multiple electrode structures as well. An electronic circuit that can be used with the specific multi-electrode structure shown in FIGS. 2a and 2b is illustrated in FIG. 3b. In this scheme, three instrumentation amplifiers 202a-202c and analog filters 204a-204c detect the differential signals collected from opposite pairs of electrodes. A multiplexer brings all three signals to a shared A/D converter 206 and radio 210 for wireless transmittal 214.

Collecting signals from opposite pairs of differential electrodes, as shown in FIG. 3b, yields the best results (highest voltages) for physiological signal vectors that are naturally aligned with one of the three major axes defined by the pairs of opposite electrodes. Although the example shows six electrodes, a patch using just four electrodes (two pairs) would produce signals that could theoretically be processed to resolve the same vectors seen with more electrodes.

Two alternatives to the signal processing approach using four electrodes are to increase the number of electrodes—for example to six, as shown here—and to measure voltages across non-opposite pairs of electrodes. A patch with six electrodes, for example, can provide a total of six axes of measurement, spaced 30 degrees apart, if non-opposite electrode pairs can be used for the measurement.

Figure 3C:
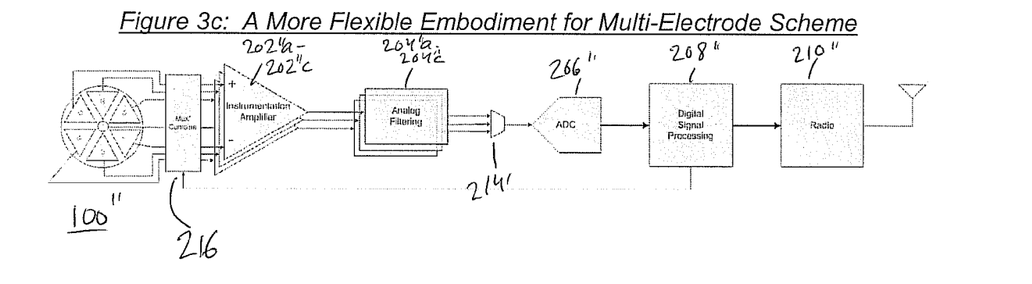
FIG. 3c is a second embodiment of a sensor coupled to multiple electrodes.

FIG. 3c is another embodiment of a multi-electrode patch system. The system adds a multiplexer circuit 216 between the electrodes of the patch 100 and the amplifiers 202a-202c. In this embodiment, all six axes can be measured, using various pairs of electrodes selected by the multiplexer. An additional benefit of including the multiplexer circuit is that it provides a reliability advantage; in the event one electrode loses contact with the skin and becomes unusable, signals from a different pair aligned along the same axis could be selected instead.

The instrumentation amplifiers shown in all three diagrams represent one embodiment for providing the gain required in the first stage of processing, but other schemes using other types of amplifiers are possible. Specifically, multiple single-ended amplifiers could be used in place of the instrumentation amplifiers, reducing cost.

The electronic circuits need to be integrated with the electrodes and battery, etc. to form the complete patch. Additional electronics (not shown in the figures) may be added to enhance the user interface, such as switches, LEDs, displays and mechanical transducers. Other circuitry not shown may be included to improve operation of the patch, such as clocks, timers, power supplies, battery chargers and test interfaces.

Although the description of the electronics above is based on the measurement of differential voltages across a pair or pairs of electrodes, the same electronics could be used to support a sensor system featuring multiple electrode sensors employed in various diagnostic testing methodologies described previously.

Patch Usability and Patient Experience

Many features of the integrated multi-electrode wireless patch are particularly attractive for long-term monitoring situations. In addition to battery operation, wireless connectivity and "single patch" application, other features are included to maximize monitoring success. If the patch is not comfortable and the patient removes it—even temporarily—any data collected may be seriously compromised.

In order for a patch to perform long-term (multiple days to weeks) monitoring, it must withstand moisture, including total immersion in water. The following lists the target design criteria (from most to least important) the patch will meet under worst-case moisture conditions, such as swimming in salt water:

1. Cause no harm to the patient
2. No damage to the patch electronics or reduction of battery life
3. Continue to adhere to the patient's skin
4. Operate normally once the patient has dried off
5. While wet, take data and store temporarily on patch
6. While wet, continue to operate normally, taking data and relaying it via radio to a Mobile Device Because of the electrical characteristics of water, the last criterion is unlikely to be met, in which case, only items 1-5 will apply. To meet these criteria will require a combination of technologies, including but not limited to:

1. Conformal coating on circuit board to protect traces and devices
2. Sealing layers of plastic to protect battery and circuits
3. Advanced adhesives and electrode gels compatible with human skin for long-term use.

The usability features detailed above contemplate electrodes placed on the skin. Additional requirements would be appropriate for electrode sensors 12a-12n placed in contact with a biological sample or tissue, immersed in a biological fluid, or placed in the vascular system or urinary tract. Additional requirements would include compatibility with blood, blood products, or urine, including resistance to clotting and durability against corrosion caused by various salts.

Additional details related to user experience are presented in the following sections.

Patch Construction

A multi-electrode wireless patch can be built in a variety of ways. Two broad categories of patch design are fully disposable and partially reusable. In the fully disposable design, the entire patch is discarded after a single use, while the reusable design retains the electronics (and optionally, the battery) and only the electrode component is discarded.

Figure 4:
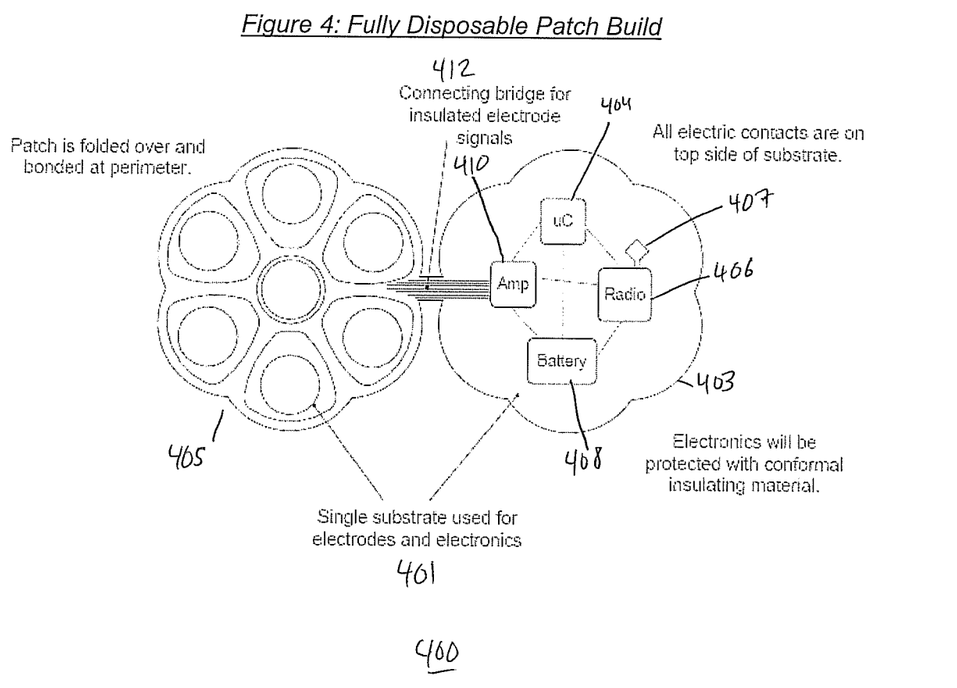
FIG. 4 is an illustration of a fully disposable multi-electrode patch.

For the fully disposable wireless patch 400, one embodiment uses a single flexible substrate 401, as shown in FIG. 4.

On the left side in the figure, electrodes 402a-402f are fabricated on the substrate while electronic components 404-410 are mounted on the right side. The connecting "bridge" 412 between the two sides includes conductors to connect the electrodes to the electronics. The patch is folded over and bonded at the perimeter. A battery 408 (not shown) may be sandwiched between the top and bottom or attached outside the substrate 401 and connected to the electronics side 403 of the patch 408. The electrode side 405 now becomes the bottom of the patch that attaches to the body. The radio antenna 407 is fabricated as part of the circuitry on the electronics side 403 of the patch 400.

For the partially reusable patch, two design variants are described here. In the first variant, the battery and electrodes are combined into a single module and the electronics is packaged as a separate manufactured unit. The two units are connected together by the patient or medical assistant at the time of the patch application. When the monitoring is complete or the battery runs out, the electrode+battery module is discarded and a new one is attached to the electronics unit for continued operation.

The second partially reusable design variant combines the electronics and a rechargeable battery in a reusable unit, with a separate disposable electrode unit. This design has the advantage of less waste, since the battery is not discarded after each use. A disadvantage of this approach is the need to recharge the battery between applications.

In both of these reusable designs, two substrates are required—one for the electrodes and the other for electronic circuits. The two substrates need to be bonded together with some type of contact scheme between the electrodes and electronics, with one such scheme described below.

Figure 5:
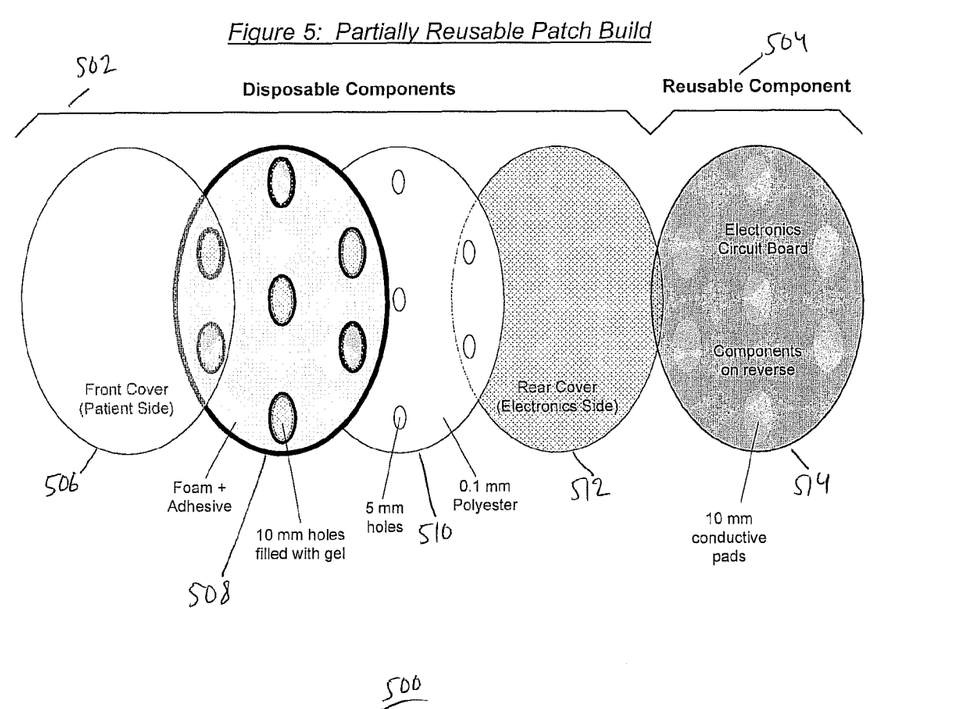
FIG. 5 shows the essential components required of both variants of the partially reusable patch for a specific design.

FIG. 5 shows the essential components required of both variants of the partially reusable patch 500 for a specific design. As is seen, there are disposable components 502 that comprises a front cover 506, an adhesive 508, a plastic member 510, and a rear cover 512, while the reusable component is a circuit board 514. The number of electrodes, size of electrodes and size of overall patch will vary with different applications.

A quantity of conductive electrode gel is placed in each of the holes in the foam and polyester sandwich 508-510 at the time of manufacture. Additionally, thin sheets of plastic 506 and 512 are applied to the front and rear of the disposable substrate to cover and protect the gel from contamination until the patch is applied. The entire sandwich comprising the disposable component will be sealed in a package during manufacture to prevent dehydration of the electrode gel.

When the patch is to be applied, the disposable component 502 will be removed from its packaging and the rear cover 512 removed. The user will then attach the electronics circuit board 514 to the exposed rear section, after aligning the conductive pads with the gel areas. The adhesion of the gel alone may be sufficiently strong to hold the circuit board to the disposable component, or additional adhesive may be applied. Lastly, the front protective liner 506 is removed, exposing the other side of the gel contacts so the patch can then be placed on the patient's skin to begin monitoring.

Because the substrate holes allow conduction between the front (patient side) and rear (electronics side) patches of gel, essentially an electric "via" is formed, but without requiring the complicated processing steps needed for making a similar structure in a conventional circuit board. Note that the use of a single circular hole per "via" in the foam 508 or polyester 510 is not a particular requirement of this scheme; different shapes as well as multiple smaller holes per contact area (rather than a single larger one) could function in the same manner and may have some technical or other advantages.

The electronics substrate in this embodiment uses conventional flexible or rigid circuit board technology. All of the components are mounted on the top side of the board, with the bottom reserved for the pattern of conductive metal that mates with the pattern of conductive gel on the disposable electrode substrate. The conductive metal pattern on the bottom is plated with a metallic preparation (typically silver-based, although other metals are possible) compatible with the gel used for the electrodes.

When the monitoring period is over, the disposable electrode sandwich 508-510 is peeled off the electronics substrate and discarded. The reusable electronics substrate 504 can then be disinfected, recharged and reapplied as required.

Because the disposable electrode substrate 502 does not require a plated silver contact area, it can potentially be very inexpensive. It also could be fabricated with biodegradable materials, such as cellulose or other organic polymers, to minimize waste handling issues.

In yet another scheme, the patch substrate can have a three dimensional profile, formed either by molding ridges into a somewhat rigid substrate, or by selectively adding layers of thicker material to a more flexible substrate. The third dimension can be used to build in features for various purposes including enhanced patient convenience and improved contact reliability.

For example, to minimize skin irritation over a long monitoring period, the patch may contact the skin only in those areas specifically where the either the electrodes or the adhesive needs to touch. Between the seven sections shown in FIGS. 2a and 2b for example, the patch could be elevated off the skin to allow air and perspiration to move freely. With sufficiently flexible substrates, these elevated "non-contacting" areas could also serve as moveable joints that improve comfort for the patient.

Another possible use for a three dimensional profile is to simplify the manufacturing process. An example is to form "wells" in the substrate to contain the gel material as it is initially applied during manufacture. The wells could also, once applied to a patient's skin, act as barriers to external contaminants.

The wireless patch presented here can be used for detecting and monitoring physiological voltage signals for various applications such as the brainwave activity (EEG), heart health (ECG), muscle performance (EMG) or a variety of other electric characteristics of the human body. These methods play important roles in emergency and acute care, long-term monitoring of chronic conditions and even normal fitness training. Wireless sensors for many other health applications can also be built by using this multiple-electrode scheme for voltage sensing. For example, a body impedance sensor can be built by injecting constant current into the body through electrodes and measuring the voltage. Impedance sensors are used to monitor a variety of human body conditions such as hydration, dehydration, tissue state, wound state, etc. Hydration measurements are used to monitor conditions such as CHF (congestive heart failure). Dehydration measurements are useful to monitor the conditions of firefighters, athletes, seniors and military personnel.

Similar design schemes can also be pursued for electrode sensors, which also can be made either fully disposable or partially disposable. For example, in a fully disposable design, a single substrate can also be used to support the sensor electrode(s) structure and the electronics in a construction that features a connecting bridge between the two. The unit may be folded, bonded, and applied to, or inserted into, a connecting receptacle integrated into a catheter or other device. In a partially reusable design, the battery and electronics can be incorporated into a reusable instrument or device. A separate disposable electrode unit can be mounted on an appropriate substrate and connected to the battery and electronics.

Multiple Electrode Patches Examples
Convenience of Placement

The electric signals to be monitored with E*G methods vary from person to person, with the voltage levels, frequency ranges and details of the waveforms, examples of some of those differences. Other measurement-instance differences can add to the variables, often making analysis considerably more difficult. Example of instance issues are electrode placement, skin preparation, electrode composition and conduction-enhancing electrolytes (such as pastes or gels), if used.

The placement of electrodes for standard diagnostic E*G methods has evolved over 150+ years to minimize the amount of variability due to placement alone. In the case of ECGs, ten electrodes are used in twelve wiring combinations to produce a standard suite of traces for analysis by medical experts trained in the method.

There are cardiac monitoring situations that do not require all ten electrode connections, such as Holter and event monitors that may use as few as two.

If the two electrodes needed for the "minimal" case are physically connected together, such as in a single adhesive patch with two conductive gel areas, and applied to the skin, the relative location of the two electrodes would require the patch be applied at a specific angle with respect to the expected signal to be measured for best signal quality. The multiple electrode structure described above simplifies placement on the body while attaining high signal quality.

Coverage of Multiple Views

In traditional multiple-lead ECG measurement systems, several wired electrodes are placed on the body to get different "views" of the potential electric vectors traveling through the body at different angles and different locations. In the multi-electrode patch scheme, in accordance with the present invention, these views are captured by using the appropriate electrode pairs within a single patch at one location. For cases where a single patch is unable to resolve all the views required, additional patches may be added to different locations on the body.

For a six electrode (plus reference ground) patch, three different views are possible by measuring the signals across opposite pairs of electrodes, as shown in FIG. 6a. Using adjacent pairs of electrodes, six more combinations are possible, but the measurement angles are all duplicates of the original three, so using adjacent pairs is less useful. However, by connecting between non-opposite, non-adjacent pairs, three more unique views are possible, bringing the total to six. As shown in the figure, the views all correspond to six of the standard measurement angles obtained from a 12-lead ECG.

FIG. 6b shows the same combination of views, but with the patch turned 60 degrees. Although the same six views are covered, this orientation may be preferable if only three views are deemed necessary for successful monitoring.

Figure 7:
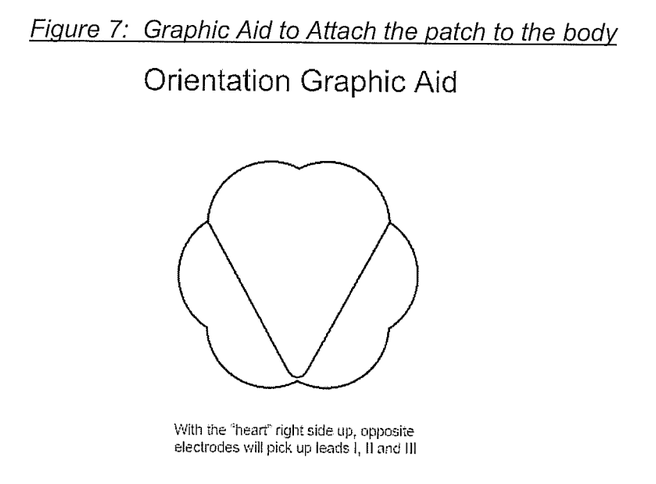
FIG. 7 is an illustration of the graphic aid to attach the patch to the body.

Even though the multi-electrode patch reduces or even eliminates the requirement for controlling the angle of placement on the patient, the complexity of the electronics and the quality of the signal could still be related factors. In addition, the patient experience could possibly be improved if there was an indication that the patch was placed "correctly", especially in a situation where it is self-applied. To address this issue, FIG. 7 shows an example of a graphic aid—a heart—imprinted on the top of the patch to help the patient orient the patch on their body.

These figures show only certain possibilities in the case of ECG. The multiple electrode schemes can be used in many other ways in case of ECG, EEG, EMG and other applications, such as an impedance sensor.

Obtaining Enhanced Physiological Signals

Another application of multiple-electrodes is the enhancement of physiological signal being monitored (e.g. ECG). The signals from multiple electrodes can be combined, and various signal processing algorithms, such as averaging and filtering can be used to enhance the quality of signal.

Electrode Sensors

Some of the measurements of physiological significance are also based on electrodes that measure a conductance change in the presence of a particular analyte. Examples include glucose, electrolytes, blood gases, and other biosensors where selectivity is based on the use of various reagents such as enzymes, proteins, or oligonucleotides. Wireless electrode sensor(s) allow for enhanced patient mobility in all settings. In acute care environments, wireless electrode sensor(s) have additional benefits: reducing the risk of hospital-acquired infections from contaminated wires; decluttering the workspace, and the reduction of signal noise introduced by the presence of wires.

All these are some of the examples of the multiple-electrode scheme to achieve various objectives of an integrated wireless physiological monitoring system. There are many other possibilities.

SUMMARY

A wireless sensor has been described that uses a fresh perspective of wireless physiological monitoring, as opposed to simply migrating the "wired links" of today's wired physiological monitoring systems to "wireless links". The invention relates to many different technologies to define a wireless sensor that is highly integrated, small, and low cost. An integrated multi-electrode scheme is proposed to attain many of these advantages. Certain manufacturing methods are proposed, and the concepts of disposable and reusable options are discussed. A sensor in accordance with the present invention can be utilized to monitor a variety of applications relating to health, disease progression, fitness and wellness. Some of the specific applications include the monitoring of ECG, EEG, EMG, glucose, electrolytes, body hydration, dehydration, tissue state and wounds.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended.

What is claimed is:

1. A sensor system comprising:
    a plane member;
    a plurality of electrodes within a first side of the plane member and adapted to contact a human body to detect and monitor human generated voltages; and
    a circuit on a second side of the plane member for providing signals over a wireless link, wherein the circuit comprises: a plurality of amplifiers for simultaneously amplifying signals received from the electrodes, wherein each amplifier of said plurality detects differential signals from different pairs of electrodes of said plurality; a plurality of filters for the signals; an analog to digital converter (ADC) for converting the signals to digital signals; a digital signal processor for processing the digital signals; and
    a radio for wirelessly transmitting the digital signals,
    wherein the plane member is folded over so the first side overlies the second side.

2. The system of claim 1 wherein the amplifiers detect differential signals from opposite pairs of electrodes.

3. The system of claim 1 which includes a multiplexer for receiving the signals from the plurality of filters and providing the signals to the analog to digital converter.

4. The system of claim 1 wherein a portion of the sensor system is disposable.

5. The system of claim 1 wherein a multiplexer is inserted between the plurality of electrodes and plurality of amplifiers.

6. The system of claim 1, wherein the plurality of electrodes are ECG electrodes.

7. The system of claim 6, wherein the amplifiers simultaneously detect differential signals from at least three pairs of electrodes.

8. The system of claim 6, wherein a stationary patient monitor or mobile device are configured to capture transmitted signals from said radio.

* * * * *

UNITED STATES PATENT AND TRADEMARK OFFICE
CERTIFICATE OF CORRECTION

PATENT NO. : 8,718,742 B2  
APPLICATION NO. : 12/601373  
DATED : May 6, 2014  
INVENTOR(S) : Beck et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 835 days.

Signed and Sealed this

Twenty-ninth Day of September, 2015

Michelle K. Lee
*Director of the United States Patent and Trademark Office*